US 011395516B2

(12) United States Patent
Paradis

(10) Patent No.: US 11,395,516 B2
(45) Date of Patent: Jul. 26, 2022

(54) SENSORY APPAREL

(71) Applicant: Lisa Paradis, West Hartford, CT (US)

(72) Inventor: Lisa Paradis, West Hartford, CT (US)

(*) Notice: Subject to any disclaimer, the term of this patent is extended or adjusted under 35 U.S.C. 154(b) by 321 days.

(21) Appl. No.: 16/527,671

(22) Filed: Jul. 31, 2019

(65) Prior Publication Data

US 2021/0030074 A1    Feb. 4, 2021

(51) Int. Cl.
| | | |
|---|---|---|
| A41B 1/18 | (2006.01) | |
| A61M 21/02 | (2006.01) | |
| A41D 27/18 | (2006.01) | |
| A41D 11/00 | (2006.01) | |
| A41D 27/08 | (2006.01) | |
| A61M 21/00 | (2006.01) | |

(52) U.S. Cl.
CPC .............. *A41B 1/18* (2013.01); *A41D 11/00* (2013.01); *A41D 27/08* (2013.01); *A41D 27/18* (2013.01); *A61M 21/02* (2013.01); *A41B 2400/32* (2013.01); *A41D 2400/32* (2013.01); *A61M 2021/0022* (2013.01); *A61M 2021/0044* (2013.01); *A61M 2209/088* (2013.01)

(58) Field of Classification Search
CPC ......... A41B 1/02; A41B 1/18; A41B 2400/32; A41B 2400/60; A41B 3/00; A41B 1/12; A41D 11/00; A41D 27/08; A41D 27/18; A41D 2400/32; A41D 13/1245; A41D 2600/00; A41D 27/20; A41D 27/205; A61M 2021/022; A61M 21/02; A61M 21/00; A61M 2209/088
See application file for complete search history.

(56) References Cited

U.S. PATENT DOCUMENTS

| | | | | |
|---|---|---|---|---|
| 2001/0054192 A1* | 12/2001 | Haar | .................... | A42B 3/0406 2/69 |
| 2015/0273178 A1* | 10/2015 | Johnson | ................ | A61M 21/02 600/27 |
| 2017/0014595 A1* | 1/2017 | Heath | ....................... | G09B 1/00 |
| 2018/0228224 A1* | 8/2018 | Radcliffe | ............. | A63B 67/002 |
| 2018/0326175 A1* | 11/2018 | Figures | .................. | A41D 27/28 |
| 2019/0060604 A1* | 2/2019 | Smith | ................... | A61M 21/02 |

FOREIGN PATENT DOCUMENTS

WO    WO-2008098882 A2 *    8/2008    ............... G09B 1/00

OTHER PUBLICATIONS

"Zorb(R)—Cuddle Plush Fabrics". Published at least as of Aug. 24, 2013. Accessed Oct. 6, 2021. https://www.cuddleplushfabrics.co.uk/fabric/zorb/ (Year: 2013).*

* cited by examiner

Primary Examiner — Jameson D Collier
Assistant Examiner — Matthew R Marchewka
(74) Attorney, Agent, or Firm — RC Trademark Company

(57) ABSTRACT

According to some embodiments, a garment includes an outer layer including a front half and a rear half and an inner layer disposed between the front half and the rear half. One or more openings allow access to an area defined between the front half and the inner layer. A plurality of sensory objects may be affixed to the inner layer and disposed in the area defined between the front half and the inner layer.

18 Claims, 4 Drawing Sheets

SENSORY APPAREL

BACKGROUND

Special needs children (e.g., children with autism, ADHD, Sensory Processing Disorder, anxiety, etc.) often fidget for sensory input as a calming mechanism to decrease anxiety. This fidgeting often becomes a distraction during school hours, when the child needs to be patient, to focus, to stay in their seats, etc. Today, parents sometimes carry tools (fidget toys or other items) that the child can hold and play with to provide comfort, decrease anxiety, and to decrease the need for fidgeting. However, parents are required to always carry these toys or other objects with them and this may be cumbersome and inconvenient for the parents. Moreover, an older child may be concerned that others will see him/her playing with these toys or other objects and this may lead to embarrassment. Fidget toys are also distracting to other students in a school setting. It would therefore be desirable to provide a comfort mechanism for a special needs child that does not rely on a parent being present, that allows the child to be discreet in their need for a fidget tool, and allows the tools to always be "on board" or present without distracting other around them (as fidgets are not removable). This provides increased independence for the child.

SUMMARY

Some embodiments described herein relate to a garment that includes an outer layer comprising a front half and a rear half and an inner layer disposed between the front half and the rear half. One or more openings may allow access to an area defined between the front half and the inner layer. A plurality of sensory objects may be affixed to the inner layer and disposed in the area defined between the front half and the inner layer. The garment may also include an absorbent collar/hood comprising one or more layers of waterproof and/or absorbent fabric layers.

DETAILED DESCRIPTION

In the following detailed description, numerous specific details are set forth in order to provide a thorough understanding of the embodiments. However, it will be understood by those of ordinary skill in the art that the embodiments may be practiced without these specific details. In other instances, well-known methods, procedures, and components have not been described in detail so as not to obscure the embodiments.

The present embodiments relate to an apparel item that may be worn by a special needs person to help calm the person when the person feels they need to fidget in response to feeling anxious, nervous, or impatient.

The present embodiments may also relate to a collar or hood comprising an absorbent layer to allow child to chew the garment, with the saliva being absorbed rather than allowing it to spread and the clothing to become wet and uncomfortable for the child which may also cause a rash. This is advantageous because special needs children may chew on clothing for sensory input, for providing a calming mechanism to decrease anxiety.

Figure 1:
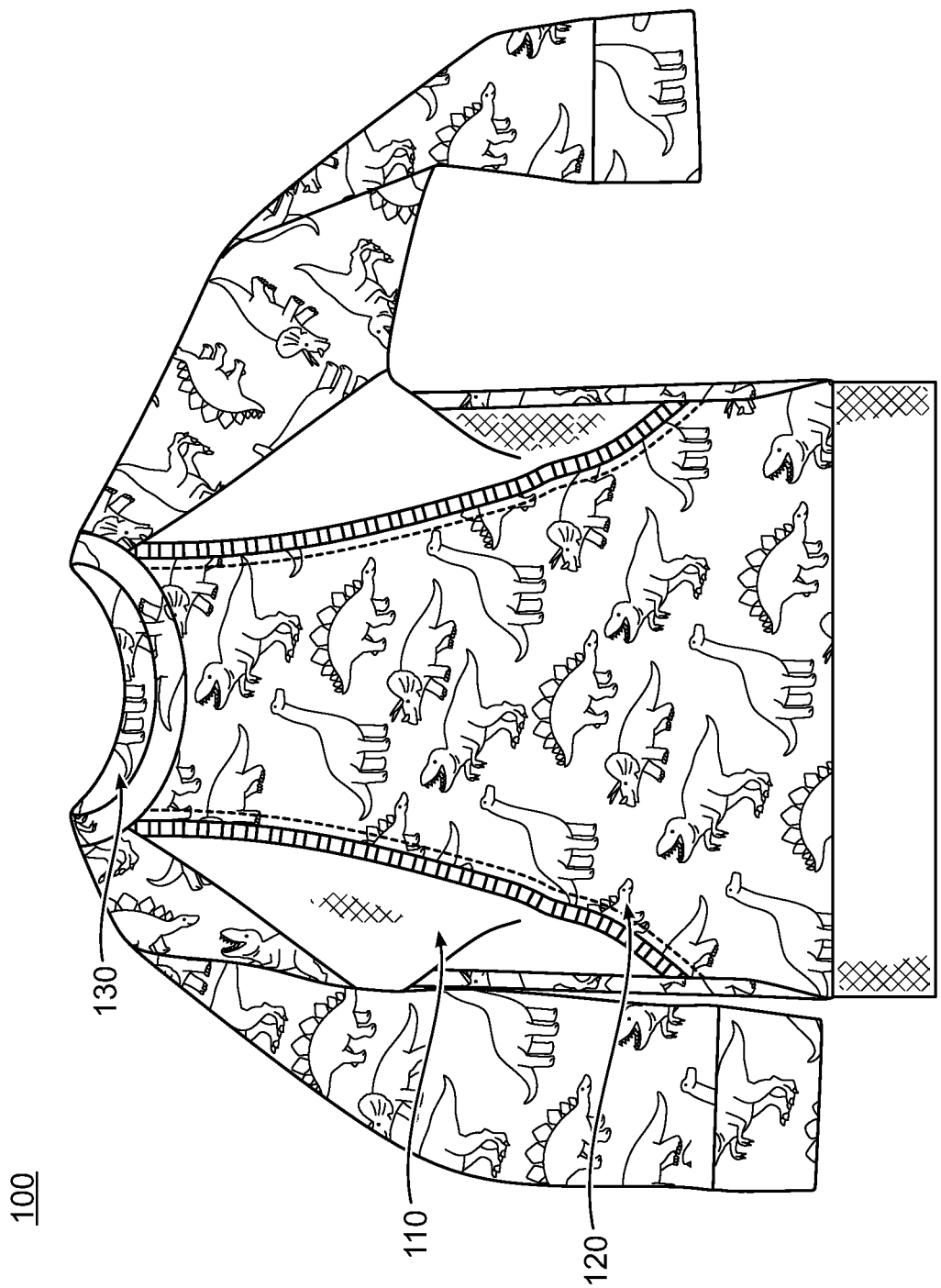
FIG. 1 illustrates a sensory apparel item in accordance with some embodiments.
Figure 3:
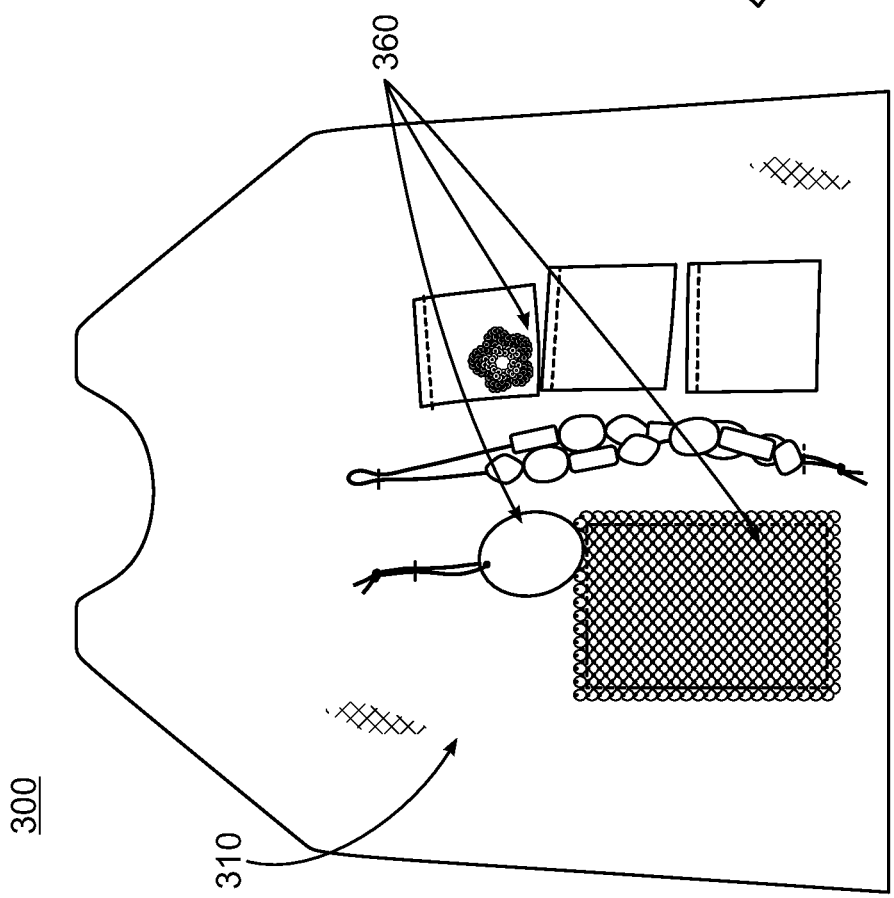
FIG. 3 illustrates a portion of a sensory apparel item in accordance with some embodiments.

Now referring to FIG. 1, an embodiment of an apparel item 100 is illustrated. The apparel item 100 may comprise a shirt, a sweater, a jacket, a sweatshirt, pants, skirt or any other item of apparel that can be adapted to the embodiments described herein. The apparel item 100 may comprise a front side 110, a back side 130 and an overlay 120 that defines an opening between the front side 110 and the overlay 120. To help a person (e.g., a child) control fidgeting, one or more sensory objects may be affixed in an area defined between the front side 110 and the overlay 120. Sensory objects may comprise, but are not limited to, one or more strings of beads, a plurality of buttons, one or more fabric pieces comprising different textures, and/or one or more sequins. In some embodiments, the sensory objects may comprise one or more sensory stones (as shown in FIG. 3) which may be defined as a stone comprising a hole (e.g., like a pendant) made from an actual stone, a stone-like material or plastic. In some embodiments, the sensory stone may comprise a smooth stone that includes a thumb indent. In other words, one or more sensory objects may be sewn on the fabric between the front side 110 and the overlay 120 for a person to use (e.g., place their hands inside the area between the front side 110 and the overlay 120 to manipulate or play with the sensory objects).

In this way, there may always be sensory objects available for a person to use for comfort and for fidgeting in response to feeling nervous or impatient. The person may simply reach into the area defined between the front side 110 and the overlay 120 to manipulate a sensory object in their hand. For example, a person who is feeling nervous may reach into the defined area to hold one or more strings of beads and the person may move the beads with their fingers. For some individual, this may provide a calming effect. Since each individual is different, different types of sensory objects may be provided. In another example, the person may move their hand over various textures of cloth that are sewn in the area between the front side 110 and the overlay 120 and this movement over various textures may provide a calming effect to the person.

Figure 2:
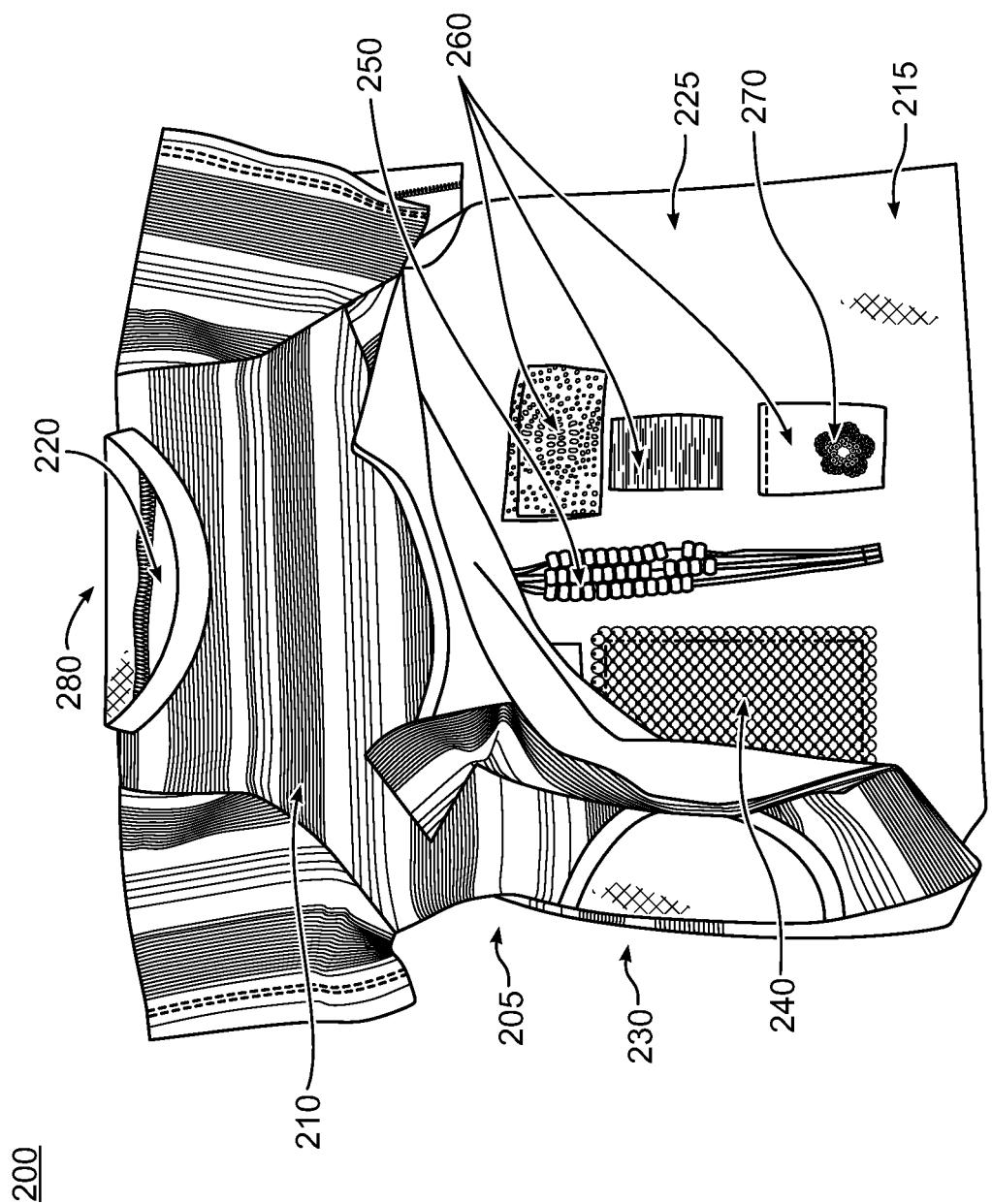
FIG. 2 illustrates a sensory apparel item in accordance with some embodiments.

Now referring to FIG. 2, an embodiment of an apparel item 200 is illustrated. The apparel item 200 may comprise a shirt, a sweater, a jacket, a sweatshirt, pants, skirt or any other item of apparel that can be adapted to the embodiments described herein.

As illustrated in FIG. 2, the apparel item 200 may comprise an outer layer 205 that includes a front half 210 and a rear half 220. The outer layer may be comprised of a cloth such as, but not limited to, cotton, wool, nylon, polyester and/or combinations thereof. An inner layer 215 may be disposed between the front half 210 and the rear half 220. The apparel item 200 may comprise one or more openings 230 to allow access to an area 225 defined between the front half 210 and the inner layer 215. For illustration purposes only, and as illustrated in FIG. 2, a portion of the front half 210 is detached to clearly show the area 225. The one or more openings 230 may be used by a wearer of the apparel to place their hands inside the area 225 to manipulate or play with the sensory objects.

The inner layer 215 may be comprised of a cloth such as, but not limited to, cotton, wool, nylon, polyester and/or combinations thereof. The inner layer 215 may extend across an entire width of the front half and each respective side of the inner layer may be sewn to the outer layer 205 at an area where the front half 210 is joined to the rear half 220. A bottom portion of the inner layer 215 may be sewn to a bottom of the front half 210. This may prevent any sensory objects from falling out of the area 225. A top portion of the inner layer 215 may be sewn across a width of the front half 210 to further define the area 225.

The apparel item 200 may comprise a plurality of sensory objects affixed to the inner layer 215 and disposed in the area 225 defined between the front half 210 and the inner layer 215. Sensory objects may comprise, but are not limited to, one or more strings of beads 250, a plurality of buttons 270, one or more fabric pieces 260 comprising different textures, and/or one or more sequins 240. The one or more fabric pieces 260 may be square or rectangular shaped and may be sewn along one side or edge of the one or more fabric pieces 260 to the inner layer to form a flap in the area 225.

As illustrated in FIG. 2, the inner layer 215 may extend at least half a length of the garment 200 (e.g., from a bottom opening of the garment to an area at, or just below, the arms or the openings for the arms).

Figure 4:
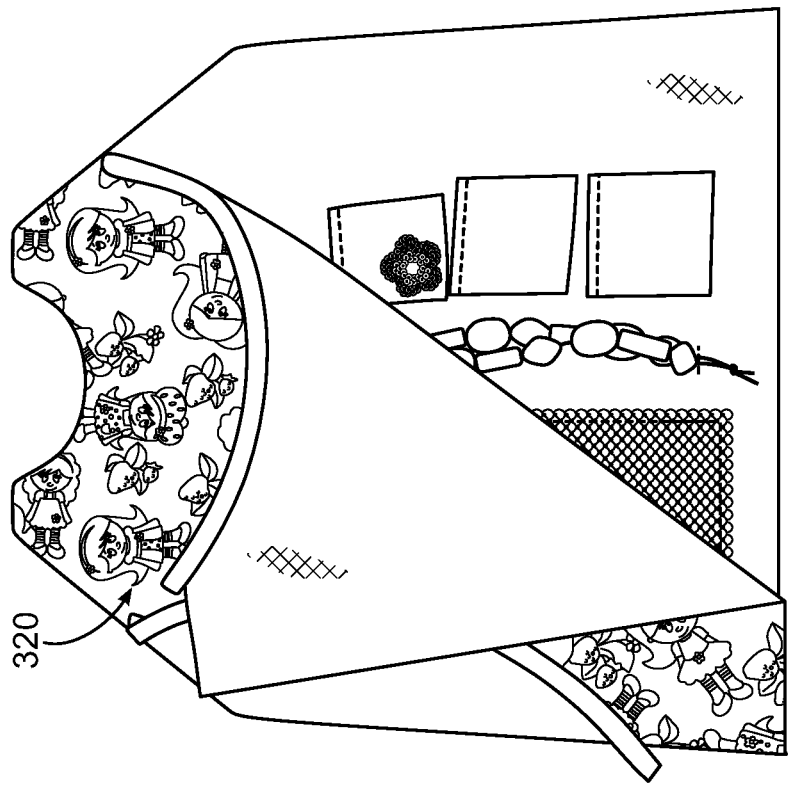
FIG. 4 illustrates a portion of a sensory apparel item in accordance with some embodiments.
Figure 5:
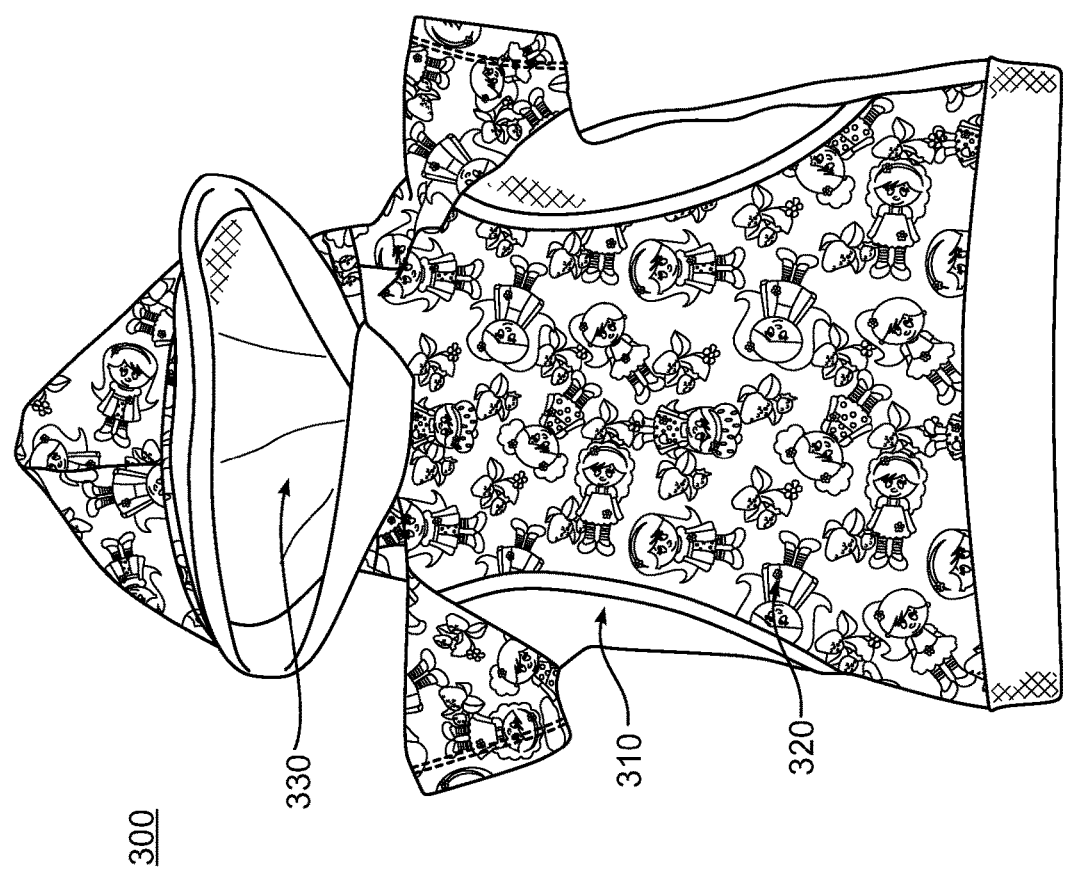
FIG. 5 illustrates a portion of a sensory apparel item in accordance with some embodiments.

Now referring to FIG. 3, FIG. 4 and FIG. 5 an embodiment of an apparel item 300 is illustrated. Apparel item 300 may comprise a front side 310 that comprises a plurality of sensory objects 360 affixed to the front side 310. As shown in FIG. 4, an overlay 320 may be placed over the front side 310 to hide the plurality of sensory object 360 and to define openings for a person to access the plurality of sensory objects 360. As illustrated in FIG. 5, the apparel item 300 may comprise a hood IQ. The hood, or in some embodiments, a collar (such as collar 280 of FIG. 2) may comprises an absorbent layer of a material. For example, the hood IQ, or a portion of the hood such as an outer edge, may comprise an outer layer of cloth that resembles a conventional outer edge but includes an inner core that is comprised of an absorbent material. The inner core may be a different material than the outer layer. The inner core may include one or more of a mixture of air-laid paper, superabsorbent polymers and/or a super absorbent fabric that absorbs 10 times its' weight in under 2 seconds such as, but not limited to, ZORB®, that may hold more liquid and dispense it quicker than conventional fabrics. In some embodiments the outer shell and the inner core may both be comprised of a super absorbent fabric that may absorb 10 times its' weight in under 2 seconds.

This written description uses examples to disclose multiple embodiments, including the preferred embodiments, and also to enable any person skilled in the art to practice the invention, including making and using any devices or systems and performing any incorporated methods. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed:

1. A garment comprising:
   an outer layer including a front half and a rear half, the front half and the rear half defining an inside area;
   an inner layer disposed between the front half and the rear half, the inner layer and the front half defining a sensory area separate from the inside area and between the front half and the inner layer;
   a plurality of sensory objects affixed to the inner layer and disposed in the sensory area defined between the front half and the inner layer; and
   one or more openings configured to allow a person's arms and hands to move from the inside area to an area exterior to the garment and then into the sensory area to access the plurality of sensory objects, wherein the inner layer extends at least half a length of the garment as measured from a topmost point of the garment to a bottommost point of the garment, and wherein the one or more openings are configured for the person's arms and hands to move from the inside area to access the plurality of sensory objects disposed in the sensory area while permitting respective intermediate portions of the person's arms to remain exterior to the garment.

2. The garment of claim 1, wherein one of the plurality of sensory objects comprises a string of beads.

3. The garment of claim 1, wherein one of the plurality of sensory objects comprises a plurality of buttons.

4. The garment of claim 1, wherein one of the plurality of sensory objects comprises one or more fabric pieces comprising different textures than the inner layer.

5. The garment of claim 4, wherein the one or more fabric pieces are square or rectangular shaped and are sewn to the inner layer along at least one side of the one or more fabric pieces to the inner layer to form a flap.

6. The garment of claim 1, wherein one of the plurality of sensory objects comprises one or more sequins.

7. The garment of claim 1, wherein the garment comprises a shirt and the plurality of sensory objects are disposed between a bottom opening of the shirt and openings for arms in the shirt.

8. The garment of claim 1, further comprising:
   a collar comprised of a super absorbent fabric that absorbs 10 times greater than a weight of the super absorbent fabric in under 2 seconds.

9. A garment comprising:
   an outer layer including a front half and a rear half, the front half and the rear half defining an inside area;
   an inner layer disposed between the front half and the rear half, the inner layer and front half defining a sensory area separate from the inside area and between the front half and the inner layer;
   a string of beads affixed to the inner layer and disposed in the sensory area defined between the front half and the inner layer;
   one or more openings configured to allow a person's arms and hands to move from the inside area to an area exterior to the garment and then into the sensory area to access the string of beads disposed in the sensory area and affixed to the inner layer between the front half and the inner layer; and
   one or more fabric pieces comprising different textures than the inner layer, the one or more fabric pieces being affixed to the inner layer and disposed in the sensory area defined between the front half and the inner layer, wherein the inner layer extends at least half a length of the garment as measured from a topmost point of the garment to a bottommost point of the garment, and the one or more openings are configured for the person's arms and hands to move from the inside area to access the sensory area while permitting respective intermediate portions of the person's arms to remain exterior to the garment.

10. The garment of claim 9, further comprising a plurality of buttons affixed to the inner layer and disposed in the sensory area defined between the front half and the inner layer.

11. The garment of claim 9, wherein the one or more fabric pieces are square or rectangular shaped and are sewn to the inner layer along at least one side of the one or more fabric pieces to the inner layer to form a flap.

12. The garment of claim 9, further comprising one or more sequins affixed to the inner layer and disposed in the sensory area defined between the front half and the inner layer.

13. The garment of claim 9, wherein the garment comprises a shirt and wherein the string of beads are disposed between a bottom opening of the shirt and openings for arms in the shirt.

14. The garment of claim 9, wherein the front half comprises the one or more openings.

15. A garment comprising:
   an outer layer including a front half and a rear half, the front half and the rear half defining an inside area;
   an inner layer disposed between the front half and the rear half that extends at least half a length of the garment as measured from a topmost point of the garment to a bottommost point of the garment, the inner layer and front half defining a sensory area separate from the inside area and between the front half and the inner layer;
   a string of beads affixed to the inner layer and disposed in the sensory area defined between the front half and the inner layer;
   one or more square or rectangular shaped fabric pieces comprising different textures than the inner layer, the one or more square or rectangular shaped fabric pieces being affixed to the inner layer and disposed in the sensory area defined between the front half and the inner layer, wherein the one or more square or rectangular shaped fabric pieces are sewn to the inner layer along at least one side of the one or more square or rectangular shaped fabric pieces to the inner layer to form a flap; and
   one or more openings configured to allow a person's arms and hands to move from the inside area to an area exterior to the garment and then into the sensory area to access the string of the beads and the one or more square or rectangular shaped fabric pieces disposed in the sensory area and affixed to the inner layer between the front half and the inner layer;
   wherein the one or more openings are configured for the person's arms and hands to move from the inside area to access the sensory area while permitting respective intermediate portions of the person's arms to remain exterior to the garment.

16. The garment of claim 15, further comprising a plurality of buttons affixed to the inner layer and disposed in the sensory area defined between the front half and the inner layer.

17. The garment of claim 15, further comprising one or more sequins affixed to the inner layer and disposed in the sensory area defined between the front half and the inner layer.

18. The garment of claim 15, wherein the garment comprises a shirt and the string of beads are disposed between a bottom opening of the shirt and openings for arms.

* * * * *